United States Patent [19]

Runciman et al.

[11] Patent Number: 5,785,712
[45] Date of Patent: Jul. 28, 1998

[54] RECONSTRUCTION BONE PLATE

[75] Inventors: Robert John Runciman, Renfrew, Canada; Randall N. Allard, Plymouth, Ind.

[73] Assignees: Terray Corporation, Ontario, Canada; Bristol-Myers Squibb Company, New York, N.Y.

[21] Appl. No.: 633,399

[22] Filed: Apr. 16, 1996

[51] Int. Cl.$^6$ ................................................. A61B 17/80
[52] U.S. Cl. ................................................. 606/69
[58] Field of Search ........................... 606/69, 70, 71, 606/61, 101, 60

[56] References Cited

U.S. PATENT DOCUMENTS

| | | |
|---|---|---|
| 1,105,105 | 7/1914 | Sherman . |
| 4,009,712 | 3/1977 | Burstein et al. . |
| 4,219,015 | 8/1980 | Steinemann . |
| 4,297,993 | 11/1981 | Harle . |
| 4,484,570 | 11/1984 | Sutter et al. . |
| 4,573,458 | 3/1986 | Lower . |
| 4,611,581 | 9/1986 | Steffee . |
| 4,683,878 | 8/1987 | Carter . |
| 4,903,691 | 2/1990 | Heinl . |
| 4,905,679 | 3/1990 | Morgan . |
| 4,905,680 | 3/1990 | Tune . |
| 4,923,471 | 5/1990 | Morgan . |
| 4,959,065 | 9/1990 | Arnett et al. . |
| 4,966,599 | 10/1990 | Pollack . |
| 5,002,544 | 3/1991 | Klaue et al. . |
| 5,041,113 | 8/1991 | Biedermann et al. . |
| 5,053,036 | 10/1991 | Perren et al. . |
| 5,108,399 | 4/1992 | Eitenmuller et al. . |
| 5,151,103 | 9/1992 | Tepic et al. . |
| 5,190,545 | 3/1993 | Corsi et al. . |
| 5,201,737 | 4/1993 | Leibinger et al. . |
| 5,269,784 | 12/1993 | Mast . |
| 5,290,281 | 3/1994 | Tschakaloff . |
| 5,372,598 | 12/1994 | Luhr et al. . |

OTHER PUBLICATIONS

"Summary: Reconstruction Plates", catalog extract, Synthes, May, 1987, p. 2–13.

*Primary Examiner*—Guy V. Tucker
*Attorney, Agent, or Firm*—Pearne, Gordon, McCoy and Granger LLP

[57] ABSTRACT

An elongated bone plate having an upper surface and a lower surface is provided along its length with at least a pair of spaced apart screw holes extending therethrough from the upper to the lower surface. The plate is provided, on at least a selected one of its upper or lower surfaces between at least one pair of the screw holes, with an indentation.

16 Claims, 1 Drawing Sheet

RECONSTRUCTION BONE PLATE

FIELD OF THE INVENTION

The present invention relates to the field of implantable orthopaedic devices. In particular, the present invention provides a novel bone plate for use with orthopaedic procedures.

BACKGROUND OF THE INVENTION

A bone plate is a strip, usually metallic, that can be attached to the surface of a bone to immobilize a fracture, or correctly position a bone or bone fragments in a reconstructive procedure. A bone plate typically is provided with a regularly spaced series of screw holes along its length, to accommodate bone screws that are used to affix the bone plate to the bone surface.

It will be readily appreciated that bones do not present a flat, planar surface. The surface contours of bones vary from bone to bone, from site to site on a bone, and between individuals. Further, since no two fractures are identical, there is often a need for considerable pre-placement shaping of a bone plate. Such shaping may be categorized as bending, which is displacement about an axis coplanar with the plate, and perpendicular to the central longitudinal axis of the plate. The shaping may be arcing, which is displacement about an axis located in a plane perpendicular to the plane of the plate, and perpendicular to the central longitudinal axis of the plate. The shaping may be classified as twisting, which is displacement helically about the central longitudinal axis of the plate. Viewed from the side, a plate that has been shaped by bending is angulated up or down. Viewed from above, a plate that has been shaped by arcing curves to the left or right.

It will be understood that prior to placement, many plates will be shaped in more than one way. If a plate were a simple rectangular strip, shaping would be a fairly straightforward, albeit highly skilled, procedure. However, the plates are typically not simple rectangular structures. The holes on a bone plate, which allow bones screws to be inserted therein weaken the plate in the areas in which the holes are formed. This can lead to several consequences. The plate can buckle during the shaping procedure or the plate can form a kink at the point of weakness or the hole can collapse so as not to be capable of accepting a screw.

It is known in the art of bone plate design, to provide inwardly directed notches between the holes to facilitate shaping. These notches lessen the amount of material—usually surgical grade steel—between the holes, and thereby tend to redistribute the stiffness of the plate along its length. Force applied to the plate to effect a shaping thereof will tend not to concentrate in the region of the holes, but can be equalized along the length of the plate, or concentrated in the spaces between the holes, as desired.

The rigidity of a plate is generally considered, and quoted, in terms of its bending and arcing functions. In respect to each of bending and arcing, the rigidity is generally measured at the narrowest point in the plate, at the level of a pair of notches. Rigidity in any particular direction will vary depending on the amount of material that must be deformed, and the extent of deformation, in the direction at issue. For instance, it will be appreciated that the provision of notches affects rigidity in both bending and arcing functions. Considering bending, providing notches will lessen the amount of material above and below the axis about which the plate is bent (such an axis is referred to as the neutral axis, because it remains relatively stationary) and thereby affect rigidity.

The effect of notches on bending will be fairly linear, as the material removed by notching is removed uniformly relative to the neutral axis of bending. That is, equal amounts of material are removed close to the axis and at extreme range from the neutral axis as a notch is formed.

The effect of forming a notch will be more pronounced, and non-linear, in relation to arcing. The neutral axis of a plate for an arcing function will be a line through the plate from top to bottom, parallel to the screw holes. Forming a notch will, therefore, reduce the total amount of material required to be deformed by the arcing process, and it will also significantly reduce the extent of deformation of the material farthest from the neutral axis—an effect that will be enhanced by forming the notches arcuately, rather than squarely.

In view of the foregoing, it will be appreciated that it is difficult to custom design a plate with enhanced bending capability, without adversely affecting arcing rigidity. Such a plate is, however, highly desirable, since the geometry of bones dictates that plates need to be bent frequently to be made to fit. This feature has heretofore been considered incompatible with high plate rigidity in the arcing direction. Moreover, since rigidity in the arcing direction has been considered as important from a therapeutic standpoint as ease of bending, plates have tended to be quite stiff in the bending direction, a feature that renders the plates difficult to work with, and can lead to hand fatigue or cramping for a surgeon having to bend one or more plates in a procedure.

The object of the present invention, therefore, is to provide a method of manufacturing a bone plate in which a desired bending rigidity may be achieved substantially without affecting arcing rigidity.

A further object of the present invention is to provide a method of controlling the rigidity of a bone plate or modifying a bone plate to reduce the bending rigidity thereof substantially without affecting the arcing rigidity thereof.

A further object of the present invention is to provide a bone plate having about the same arcing rigidity as a similarly dimensioned conventional bone plate, but with bending rigidity that has been reduced by a desired amount.

In a broad aspect, therefore, the present invention relates to a bone plate comprising a strip of metallic material having an upper surface and a lower surface, provided along its length with at least a pair of spaced apart screw holes extending through the metallic material from the upper to the lower surface, said strip being provided, on at least a selected one of its upper or lower surfaces between at least a pair of said screw holes, with an indentation to control the shaping characteristics of the plate. The indentation may be centrally located on the selected surface between the pair of holes, and may be cooperatively aligned with a pair of inwardly directed notches between the pair of holes to control the shaping characteristics of the plate.

In another broad aspect, the present invention relates to a method of manufacturing a bone plate which includes forming a least a pair of screw holes in an elongated strip of metallic material having an upper and a lower surface, the improvement comprising forming at least one indentation on a selected one of said upper and lower surfaces, between a pair of said screw holes.

In yet another broad aspect, the present invention relates to a method of controlling the rigidity of a bone plate or modifying a bone plate that includes at least a strip of metallic material having an upper surface and a lower surface with at least a pair of spaced apart screw holes extending through said strip from said upper surface to said lower surface, comprising forming at least one indentation in at least one of said upper or lower surfaces of said strip, between at least a pair of said screw holes.

BRIEF DESCRIPTION OF THE DRAWINGS

In drawings that illustrate the present invention by way of example.

DETAILED DESCRIPTION

The drawings illustrate the present invention by showing a five-hole straight line plate. It will be understood that the plate of the present invention may be of any desired length, and may be branched, curved, T-shaped, V-shaped, or any other shape, and that the dimple feature 4 may be provided between each adjacent pair of screw holes 2, or between only one pair, or several pairs of adjacent screw holes, depending on the bending characteristics desired.

Figure 1:
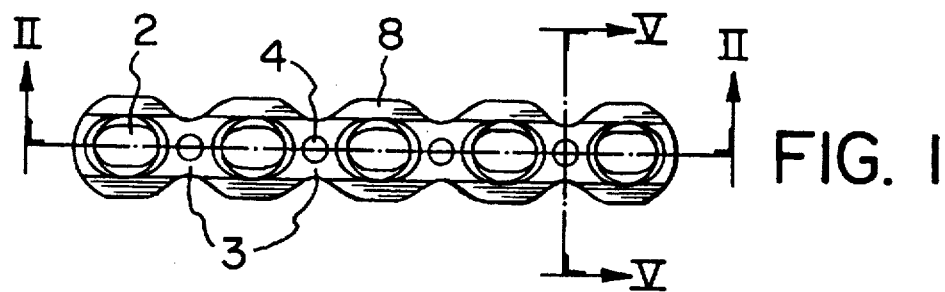
FIG. 1 is a plan view of a bone plate according to the present invention.
Figure 2:
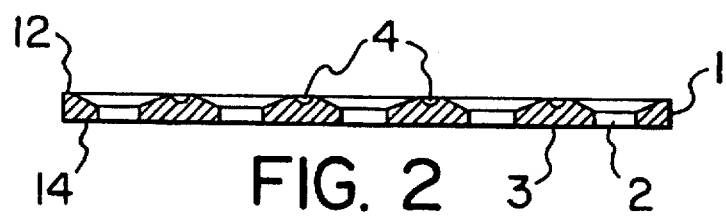
FIG. 2 is a sectional view through line II—II of the plate shown in FIG. 1.

Referring to FIG. 1, a bone plate 1 is made from an implantable material such as surgical grade stainless steel, titanium, or any other suitable material, the selection of which will be a matter of choice for one skilled in the art. A series of screw holes 2 are provided along the length of the plate. The exact geometry of each hole is not the subject of the present invention, and it will be understood that many variations in screw hole geometry, are possible, depending on the exact surgical purpose to which the plate is being put.

As illustrated in FIGS. 1–4, between the holes 2, notches 3 are formed, the function of which is to reduce the quantity of plate material between the holes 2, so that stresses associated with shaping of the plate are not concentrated at the material around the holes 2.

Figure 3:
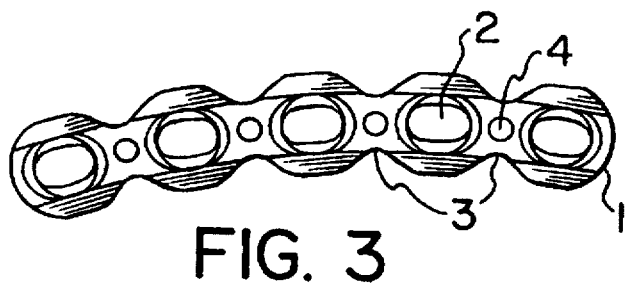
FIG. 3 is a plan view of the plate shown in FIG. 1, after having been subject to arcing.
Figure 4:
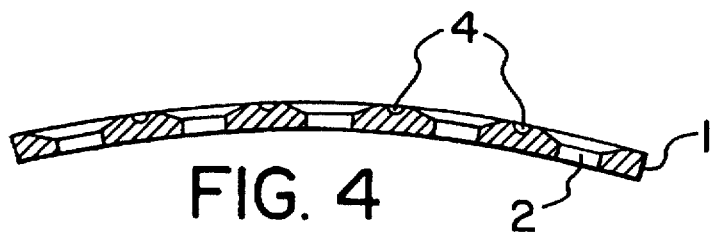
FIG. 4 is a sectional view of the plate shown in FIG. 2, after having been subject to bending.

The two shaping procedures of importance in connection with the present invention are shown in FIGS. 3 and 4, arcing, and bending, respectively. In an arcing procedure, the plate is displaced generally around neutral axis 5, shown in FIGS. 5 and 6. Such an axis 5 can be considered as existing between each pair of holes 2.

Figures 5, 6:
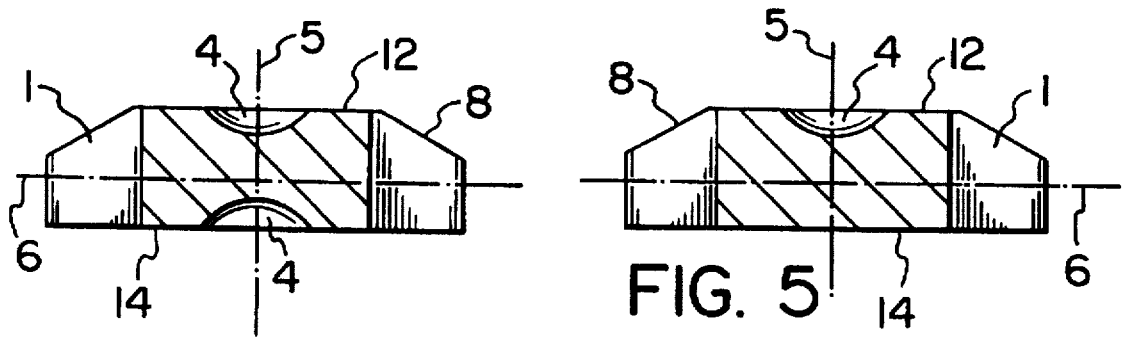
FIG. 5 is a sectional view through line V—V in FIG. 1, illustrating the bending neutral axis, and the arcing neutral axis, of the plate of FIG. 1.
FIG. 6 is an alternative sectional view similar to FIG. 5, but illustrating an indentation 4 on the upper and lower surface of the plate.

In a bending procedure, the plate is displaced generally around neutral axis 6, shown in FIGS. 5 and 6. Such an axis 6 can be considered as being present between each pair of holes 2.

The present invention resides in the provision of an indentation or a dimple 4 between pairs of holes 2, either each pair of holes, as illustrated, or selected pairs of holes. The dimple 4 which is preferably a concave shape may be provided on the upper surface 12 of the plate, as illustrated in FIGS. 1–5, on the lower surface 14 thereof, as illustrated in FIG. 6, or on both the upper and lower-surface, as shown in FIG. 6. However, any suitable size or shape may be utilized for the indentation.

As can best be seen in FIG. 5, when one considers the neutral axis for arcing 5, the rigidity of the plate will be determined by the amount of material to the left and the right of axis 5, and the distance of that material from the axis. Generally speaking, in a three dimensional system, material furthest from the neutral axis has a greater effect on the rigidity of the system than material close to the axis, since material furthest from the axis must deform to a greater extent than material close to the axis. When dealing with a material, such as steel, that has high tensile strength, the effect of material a greater distance from the neutral axis is correspondingly enhanced. As will be observed from FIG. 5, however, when one considers the placement of dimples 4, it will be observed that they are provided directly on the neutral axis for arcing 5. Therefore, the forming of dimples 4 has little or no substantial effect on the rigidity of the plate 1 about arcing neutral axis 5. It will be understood, moreover, that the dimples in a preferred embodiment be placed equidistant from adjacent holes, and aligned with the central longitudinal axis of the plate. Centering the dimples in this way ensures that the plate will bend in a predictable manner. The plate 1 may also include a downwardly sloped surface 8, as shown in FIGS. 5 and 6, along the outer edges of the upper surface of the plate. This reduces the amount of material at this portion of the plate.

About axis 6, which is the neutral axis for bending, the forming of dimples 4 removes material at a relatively greater distance away from the axis. This has a greater effect on the rigidity than removal of material close to the axis, or removal of material uniformly from the plate, as is the case, relative to the neutral axis for bending 6, in the formation of notches 3. Therefore, the formation of a dimple 4 on the upper or lower surface of the plate will affect bending rigidity substantially, with little effect on arcing rigidity.

The relative effect on bending and arcing rigidity of providing a dimple 4 is illustrated by the following table, which presents rigidity or section modulus, expressed as rigidity Z. The rigidity measurements were taken on a representative plate having holes designed to accept 3.5 mm screws.

TABLE I

| RIGIDITY MEASUREMENTS, 3.5 mm RECONSTRUCTION PLATE | | |
|---|---|---|
| | NOTCH REGION WITHOUT DIMPLE | NOTCH REGION WITH DIMPLE ON TOP |
| $Z_{Bending}$ | 7.5 mm$^3$ | 6.0 mm$^3$ |
| $Z_{Arcing}$ | 14.4 mm$^3$ | 14.3 mm$^3$ |

It will be observed, therefore, that by providing a single dimple on the top surface of a plate between two adjacent holes, rigidity in the notch region is decreased by about 20% in the bending direction, but by less than 1% in the arcing direction. This effect can be enhanced by provision of a larger dimple, or provision of a dimple on each of the upper and lower surfaces. Moreover, if one wishes to have a plate with varying bending stiffness along its length, this is easily accomplished according to the present invention, by the machining in of dimples of appropriate width and depth which may vary, as desired, or the non-provision of a dimple, between any given pair of screw holes. Such a rigidity-tailored plate is useful for instance, in long bone fixation, where the end of a plate may require extensive bending, but a more rigid central section is desired to traverse a break, followed by a less rigid section.

It is to be understood that the examples described above are not meant to limit the scope of the present invention. It is expected that numerous variants will be obvious to the person skilled in the field of implantable bone fixation and fracture stabilization device design without any departure from the spirit of the invention. The appended claims, properly construed, form the only limitation upon the scope of the invention.

What is claimed is:

1. An elongated metallic bone plate having an upper surface, a lower surface, and side surfaces, provided along its length with at least a pair of spaced apart screw holes extending therethrough from the upper to the lower surface, wherein said plate is provided, on at least a selected one of its upper or lower surfaces between at least one pair of said screw holes, with an indentation extending into but not through said plate, whereby said indentation substantially reduces the bending rigidity of said plate in the direction normal to the longitudinal axis and normal to the upper and lower surfaces thereof, but said indentation does not substantially affect the arcing rigidity of said plate in the direction normal to the longitudinal axis and parallel to the upper and lower surfaces, said indentation having a perimeter non-intersecting with adjacent screw holes and non-intersecting with said side surfaces.

2. A bone plate as claimed in claim 1, wherein there is a pair of inwardly directed notches formed in said plate between said one pair of said screw holes.

3. A bone plate as claimed in claim 2, wherein the provision of said indentation in cooperation with said pair of notches decreases bending rigidity in the area of said pair of notches by about 20%, and decreases arcing rigidity in the area of said pair of notches by less than 1%.

4. A bone plate as claimed in claim 2, wherein the provision of said indentation in cooperation with said pair of notches decreases bending rigidity in the area of said pair of notches.

5. A bone plate as claimed in claim 1, wherein said indentation or indentations are round.

6. A bone plate as in claim 5, wherein said indentation or indentations are concave dimples.

7. A bone plate as claimed in claim 1, wherein said indentation or indentations are centered on the upper or lower surfaces of said plate spaced an equal distance between adjacent screw holes.

8. A bone plate as claimed in claim 1, wherein an indentation is provided on the upper surface of said plate between every adjacent pair of screw holes.

9. A bone plate as claimed in claim 1, wherein an indentation is provided on the lower surface of said plate between every adjacent pair of screw holes.

10. A bone plate as claimed in claim 1, wherein an indentation is provided on the upper and lower surfaces of said plate between every adjacent pair of screw holes.

11. A bone plate as claimed in claim 8, 9 or 10, wherein there is a pair of inwardly directed, notches formed in said plate between each said adjacent pair of screw holes.

12. A bone plate as claimed in claim 1, wherein the plate includes a downwardly sloped surface along the outer edges of the upper surface of the plate.

13. A bone plate as claimed in claim 1, wherein said indentation has a diameter and each of said screw holes has a diameter, said indentation diameter being smaller than each of said screw hole diameters.

14. A bone plate as claimed in claim 1, wherein said plate has a first indentation between a first pair of spaced apart screw holes and a second indentation between a second pair of spaced apart screw holes, said first indentation having a size which is different from said second indentation in order to provide a varied stiffness along said plate.

15. A bone plate as claimed in claim 1, wherein the provision of said indentation decreases bending rigidity in the area of said indentation by about 20%, and decreases arcing rigidity in the area of said indentation by less than 1%.

16. A bone plate as claimed in claim 1, said plate having an indentation between each pair of a plurality of pairs of spaced apart screw holes, said indentations being selectively sized and provided to control the desired bending rigidity of said plate.

* * * * *

UNITED STATES PATENT AND TRADEMARK OFFICE
CERTIFICATE OF CORRECTION

PATENT NO. : 5,785,712
DATED : July 28, 1998
INVENTOR(S) : Robert John Runciman, et al.

It is certified that error appears in the above-identified patent and that said Letters Patent is hereby corrected as shown below:

On the title page, insert the following to item [56],

| | | | |
|---|---|---|---|
| 4,364,382 | 12/1982 | Mennen | 606/69 |
| 5,015,248 | 5/1991 | Burstein, et al. | 606/74 |
| 5,057,111 | 10/1991 | Park | 606/69 |
| 5,346,492 | 9/1994 | Morgan | 606/60 |
| 5,413,577 | 5/1995 | Pollock | 606/69 |
| 5,527,311 | 6/1996 | Proctor | 606/61 |
| 5,545,164 | 8/1996 | Howland | 606/61 |

Column 3, line 65, "lower-surface" should be --lower surface--.

Col. 4, line 64, "useful" should be --useful,--.

Col. 6, line 15, claim 11, "directed," should be --directed--.

Signed and Sealed this

Twenty-seventh Day of October, 1998

BRUCE LEHMAN

*Attest:*

*Attesting Officer*    *Commissioner of Patents and Trademarks*